US010555692B2

(12) United States Patent
Seo et al.

(10) Patent No.: US 10,555,692 B2
(45) Date of Patent: Feb. 11, 2020

(54) METHOD FOR SENSITIVELY AND SELECTIVELY SENSING SUGARS USING TERAHERTZ ELECTROMAGNETIC WAVES AND DEVICE USED THEREFOR

(71) Applicant: KOREA INSTITUTE OF SCIENCE AND TECHNOLOGY, Seoul (KR)

(72) Inventors: Min-Ah Seo, Seoul (KR); Dong-Kyu Lee, Seoul (KR); Jae-Hun Kim, Seoul (KR); Chul-Ki Kim, Seoul (KR); Taik-Jin Lee, Seoul (KR); Young-Min Jhon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 960 days.

(21) Appl. No.: 15/079,592

(22) Filed: Mar. 24, 2016

(65) Prior Publication Data
US 2017/0079563 A1    Mar. 23, 2017

(30) Foreign Application Priority Data

Sep. 23, 2015    (KR) .......................... 10-2015-0134858

(51) Int. Cl.
*A61B 5/145*    (2006.01)
*A61B 5/05*    (2006.01)

(52) U.S. Cl.
CPC ........ *A61B 5/14532* (2013.01); *A61B 5/0507* (2013.01); *A61B 2560/0412* (2013.01)

(58) Field of Classification Search
CPC .............. A61B 5/14532; A61B 5/0507; A61B 2560/0412; A61B 5/145; A61B 5/14507; A61B 5/1451; A61B 5/14514; A61B 5/05; G01J 5/20; G01J 5/22

USPC ................................................... 600/309, 365
See application file for complete search history.

(56) References Cited

U.S. PATENT DOCUMENTS

| 2011/0220799 | A1* | 9/2011 | Kim ................... H01Q 15/0086 250/338.1 |
| 2015/0276489 | A1* | 10/2015 | Cumming ............. G01J 5/0881 250/338.3 |
| 2016/0051171 | A1* | 2/2016 | Pikov ................. A61B 5/14532 600/365 |

FOREIGN PATENT DOCUMENTS

KR    20030004933 A    1/2003

OTHER PUBLICATIONS

Park et al., "Colossal Absorption of Molecules Inside single Terahertz Nanoantennas", Nano Letter, pp. 1782-1786, 2013.*
Garcia-Vidal et al., Light Passing through Subwavelength Aperatures, Rev. Mod. Phys., vol. 82, No. 1, pp. 727-787, 2010.*
(Continued)

*Primary Examiner* — Navin Natnithithadha
(74) *Attorney, Agent, or Firm* — Goldilocks Zone IP Law

(57) ABSTRACT

Disclosed herein are a method and a device for sensing sugars, using terahertz electromagnetic waves. By the method, even a trace amount of sugars in a liquid state can be accurately discriminated and sensed, with high sensitivity and selectivity, using a sensing chip that works in a terahertz electromagnetic wave band. Using the method, sugars even at low concentrations can be accurately analyzed with high sensitivity and selectivity in which terahertz electromagnetic waves are irradiated onto sugars through a sensing chip having a meta unit in which a pattern is formed to amplify a frequency corresponding to an absorption frequency of a sugar of interest.

11 Claims, 6 Drawing Sheets

(56) References Cited

OTHER PUBLICATIONS

Withayachumnakul et al., Metamaterials in the THz regime, IEEE Photonics Journal, vol. 1, No. 2, pp. 99-118, 2009.*
Son et al., "Terahertz Spectroscopy of d-Glucose", Terahertz Biomedical Science and Technology, CH 9.4, pp. 166-169, CRC Press, 2014.*

* cited by examiner

METHOD FOR SENSITIVELY AND SELECTIVELY SENSING SUGARS USING TERAHERTZ ELECTROMAGNETIC WAVES AND DEVICE USED THEREFOR

CROSS REFERENCE TO RELATED APPLICATION

The present application claims the benefit of Korean Patent Application No. 10-2015-0134858 filed on Sep. 23, 2015.

BACKGROUND OF THE INVENTION

1. Field of the Invention

The present disclosure relates to a method and a device for sensing sugars, using terahertz electromagnetic waves. Particularly, the present disclosure relates to a method by which even a trace amount of sugars in a liquid state can be accurately discriminated and sensed, with high sensitivity and selectivity, using a sensing chip that works in a terahertz electromagnetic wave band, and to a device therefor. More particularly, the present disclosure relates to a method for accurately analyzing sugars even at low concentrations, with high sensitivity and selectivity, in which terahertz electromagnetic waves are irradiated onto sugars through a sensing chip having a meta unit in which a pattern is formed to amplify a frequency corresponding to an absorption frequency of a sugar of interest, and a device therefor.

2. Description of the Related Art

For treatment, management, or diagnosis of diabetes, one of the most common diseases in people, precise measurement of blood sugar levels is very important. Unable to discriminate various kinds of sugars (e.g., sucrose, fructose, etc.) ingested along with foods, most of the currently used devices frequently output erroneous measurements of blood sugar levels before and after meals. As a solution to this problem, highly sensitive sensors for measuring blood sugar levels have been developed as described in the following patent document.

Patent Document

Korean Patent Unexamined Application Publication No. 10-2003-0004933 (issued Jan. 15, 2003) "Glucose Strip Sensor and Glucose Measurement Method by the Strip Sensor"

The selective measurement of sugars has been suggested in order to sense blood sugar levels with high sensitivity. However, the selective measurement of sugars is very difficult to achieve because various sugars are similar in molecular structure. For this, conventional sensors for measuring blood sugar levels are adapted to employ highly concentrated samples. This, however, means that a blood sample should be concentrated to a very high degree (100-fold or higher), compared to an actual blood level. Accordingly, there is an increasing need for an apparatus and a method by which precise blood sugar levels can be selectively measured even at a concentration as low as in an actual blood condition without conventional concentration.

SUMMARY OF THE INVENTION

Accordingly, the present invention has been made keeping in mind the above problems occurring in the related art, and an object of the present disclosure is to provide a method by which even a trace amount of sugars in a liquid state can be accurately discriminated and sensed, with high sensitivity and selectivity, using a sensing chip that works in a terahertz electromagnetic wave band, and a device therefor.

Another object of the present disclosure is to provide a method for accurately analyzing sugars even at low concentrations, with high sensitivity and selectivity, in which terahertz electromagnetic waves are irradiated onto sugars through a sensing chip having a meta unit in which a pattern is formed to amplify a frequency corresponding to an absorption frequency of a sugar of interest, and a device therefor.

In order to accomplish the above objects, a method and a device for sensitively and selectively sensing sugars using terahertz electromagnetic waves, have the following constitutions.

An aspect of the present disclosure provides a method for sensitively and selectively sensing sugars, using a sensing chip, wherein the sensing chip has a meta unit in which a pattern is formed for amplifying a frequency corresponding to an absorption frequency of a sugar of interest, and wherein the sensing chip, when irradiated with terahertz electromagnetic waves, passes the waves therethrough to the sugar of interest and amplifies waves reflected from the sugar of interest, whereby the sugar of interest can be analyzed for kind and concentration even when it is present at a low concentration.

In a particular embodiment, the method comprises: a target preparation step in which the sugar of interest is distributed on a sensing chip having a meta unit in which a pattern is formed for selectively amplifying a specific frequency; a light irradiation step in which terahertz electromagnetic waves are irradiated to the sugar of interest on the meta unit; and a sugar determination step in which the terahertz electromagnetic waves passing through the sensing chip are measured for transmittance or frequency change to specify sugars and to determine concentrations of the specified sugars.

In another particular embodiment, the method comprises: a chip disposition step in which the sensing chip having a meta unit in which a pattern is formed for selectively amplifying a specific frequency is positioned on the skin beneath which a vessel runs; a light irradiation step in which terahertz electromagnetic waves are irradiated onto the vessel through the sensing chip; and a sugar determination step in which terahertz electromagnetic waves that are reflected from blood of the vessel and pass through the sensing chip are measured for transmittance or frequency change to specify sugars and to determine concentrations of the specified sugars.

In the method according to some particular embodiments, the sugar determination step is adapted to measure the terahertz electromagnetic waves passing through the meta unit for transmittance or frequency change thus to specify sugars and to determine concentrations of the specified sugars, based on the fact that transmittance or a frequency change is elevated when the absorption frequency of a target sugar corresponds to the resonant transmission frequency of the meta unit.

In the method according to some particular embodiments, the pattern is in a form of slits, each penetrating through the meta unit.

In the method according to some particular embodiments, each of the slits ranges in width 10 nm to 1 um, in thickness from 100 nm to 1 um, and in length from 10 um to 1 mm.

In the method according to some particular embodiments, the pattern is an array of slits that is formed at regular gaps in the meta unit.

In the method according to some particular embodiments, the slits in the array are arranged at regular gaps of 1 nm to 1 mm in a widthwise direction and 1 nm to 1 mm in a lengthwise direction.

Another aspect of the present disclosure provides a device for sensing sugars, using the sensing chip used in the method of any one of claims 1 to 3.

In the device according to some embodiments, the sensing chip comprises: a transparent substrate that transmits terahertz electromagnetic waves therethrough; and a meta unit, positioned on one side of the substrate, in which a pattern is formed to selectively amplify a frequency of interest.

In the device according to some embodiments, the pattern is in a form of slits, each penetrating through the meta unit.

In the device according to some embodiments, each of the slits ranges in width 10 nm to 1 um, in thickness from 100 nm to 1 um, and in length from 10 um to 1 mm.

In the device according to some embodiments, the pattern is an array of slits that is formed at regular gaps in the meta unit.

In the device according to some embodiments, the slits in the array are arranged at regular gaps of 1 nm to 1 mm in a widthwise direction and 1 nm to 1 mm in a lengthwise direction.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Below, a description will be given of some embodiments of the present invention in conjunction with the accompanying drawings. Unless otherwise defined, the meaning of all terms including technical and scientific terms used herein is the same as that commonly understood by one of ordinary skill in the art to which the present invention belongs. It will be further understood that terms, such as those defined in commonly used dictionaries, should be interpreted as having a meaning which is consistent with their meaning in the context of the relevant art and the present disclosure, and will not be interpreted in an idealized or overly formal sense unless expressly so defined herein. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present disclosure, the description thereof will be omitted. Unless the context clearly requires otherwise, throughout the description and the claims, the words "comprise", "comprising", and the like are to be construed in an inclusive sense as opposed to an exclusive or exhaustive sense, that is to say, in the sense of "including, but not limited to."

The present disclosure addresses a method for sensitively and selectively sensing sugars using terahertz electromagnetic waves. The method is described in detail with reference to FIGS. 1 to 6. The method is adapted to accurately analyze sugars in a liquid state even at low concentrations, with high sensitivity and selectivity, in which terahertz electromagnetic waves (hereinafter referred to as "terawaves") are irradiated onto sugars through a sensing chip having a meta unit in which a pattern is formed to amplify a frequency corresponding to an absorption frequency of a sugar of interest.

Figure 1:
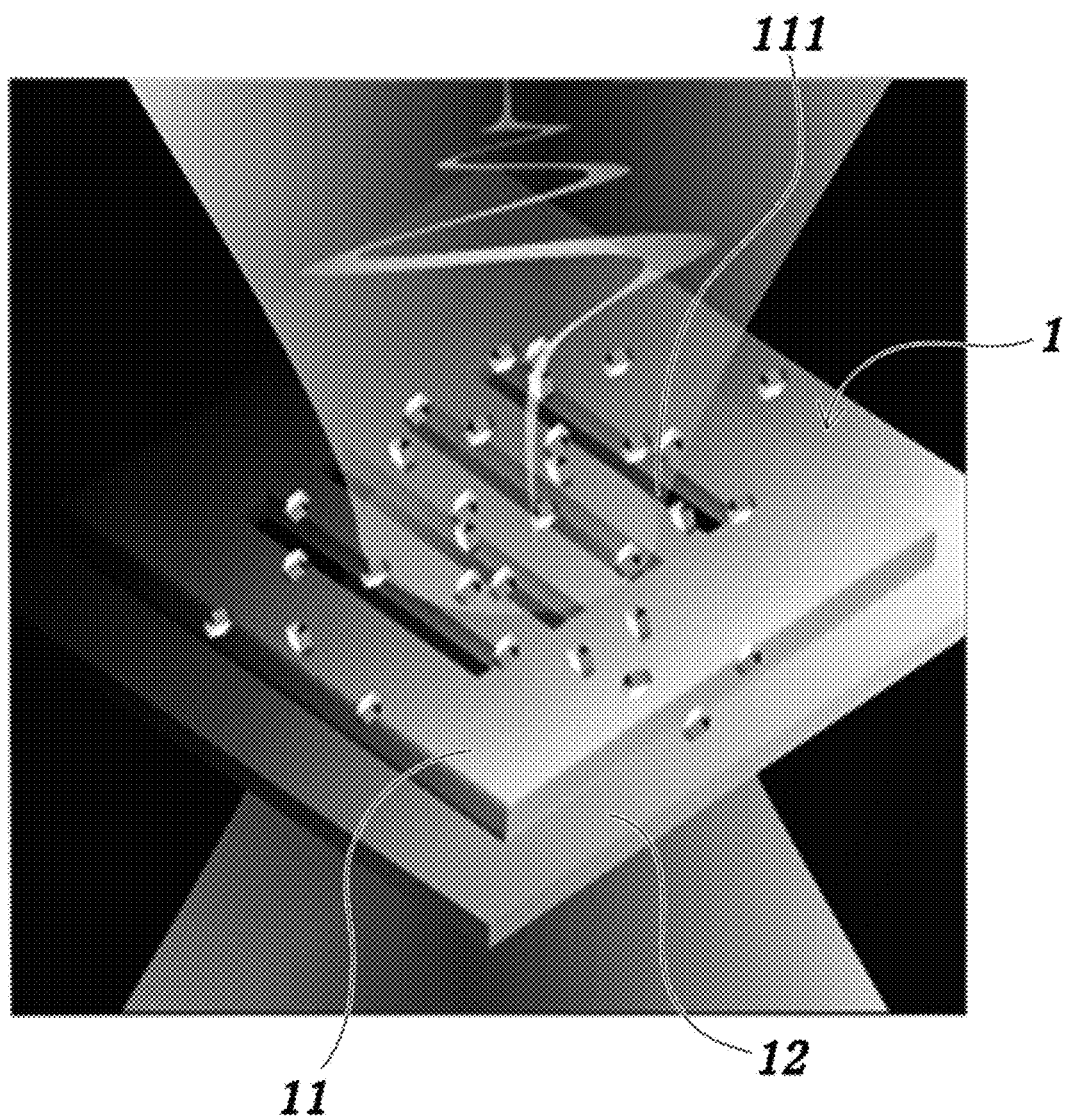
FIG. 1 is a view illustrating a method for sensing sugars in accordance with an embodiment of the present disclosure.
Figure 2:
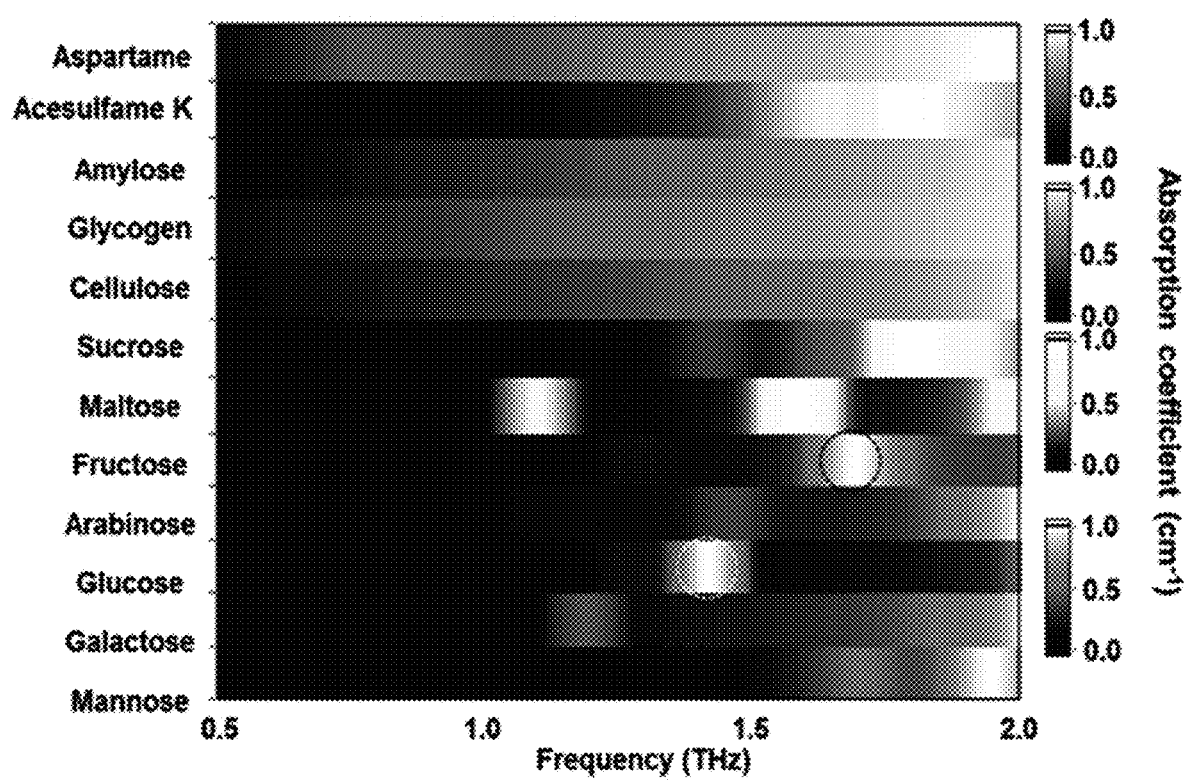
FIG. 2 is a view showing absorption spectra in a terahertz frequency band of various sugars.

As described above, it is very difficult to selectively measure concentrations of sugars because of their structural similarity. In the present disclosure, a sensing chip 1 having a meta unit 11 in which patterns are formed to amplify an absorption frequency of a sugar of interest is used to irradiate terawaves onto sugars in respective low concentrations and to selectively measure the concentration of the sugar of interest. Sugars are slightly different in molecular formula from one to another so that they show respective characteristic absorption spectra in a terahertz frequency band. As shown in FIG. 2, sugars have absorption peaks at their on characteristic frequencies. For example, absorption peaks are read at 1.43 THz for D-glucose, found in blood, at 1.8 THz for sucrose, found in foods, and at 1.7 THz for fructose, found in beverages. To selectively measure the concentration of a sugar of interest even when its concentration is low, the present disclosure takes advantage of the fact that sugars exhibit respective characteristic absorption peaks in a terahertz frequency band. In this regard, a meta unit 11 is designed such that it transmits terawaves and amplifies a frequency corresponding to the characteristic absorption frequency of a sugar of interest. Based on this principle, a target in a liquid state can be selectively measured among various sugars, and can be quantitatively analyzed even at a low concentration.

Now, a description will be given of a device useful in the method for sensing sugars. The device comprises a sensing chip 1 having a meta unit 11 that works in a terawave range, an irradiator (not shown) for irradiating terawaves onto the sensing chip 1, a detector (not shown) for measuring a transmittance and/or a frequency change of the terawaves passing through the sensing chip 1 to specify sugars and to determine concentrations of the specified sugars.

The sensing chip 1 is configured to work in a terawave range, and comprises a meta unit 11 in which a pattern is formed to selectively amplify a frequency of interest, and a transparent substrate 12 for supporting the meta unit 11.

Figure 3:
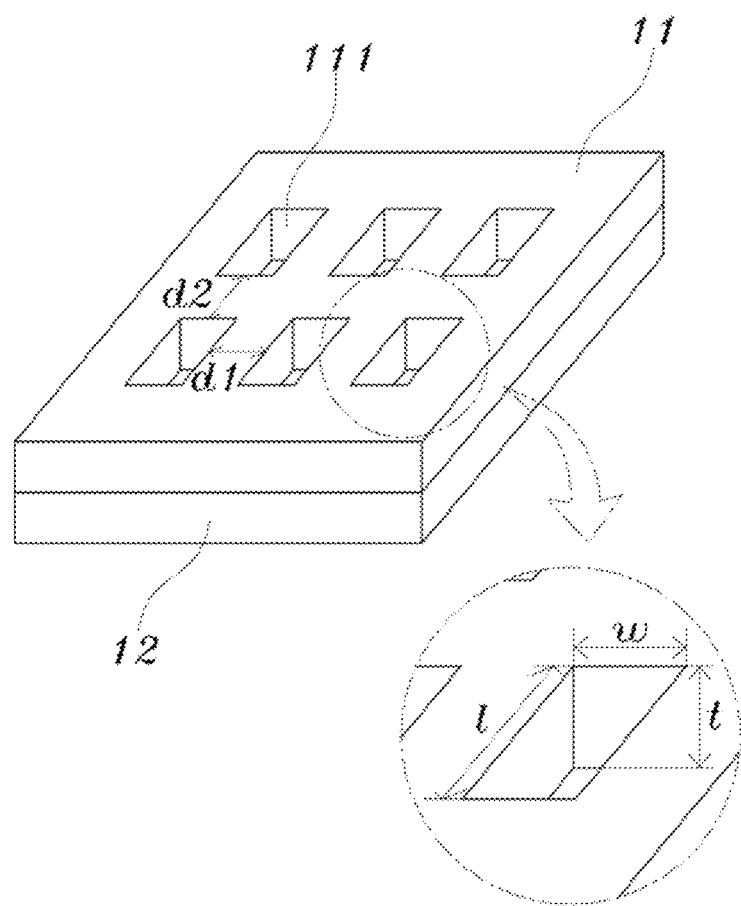
FIG. 3 is a perspective view of a sensing chip used in a method for sensing sugars in accordance with an embodiment of the present disclosure.

The meta unit 11 is configured to have a pattern 111 for selectively amplifying a frequency of interest. For example, the pattern 111 may be an array of slits that is formed at regular gaps in the meta unit, each penetrating through the meta unit, as shown in FIG. 3. The meta unit 11 may be preferably made of a metallic material, such as gold, silver, copper, aluminum, etc. In the pattern 111, the slits are constant in shape, size, and gap (hereinafter referred to as "spec"). Preferably, the slits range in width from (w) 10 nm to 1 um, in thickness (t) from 100 nm to 1 um, and in length (l) from 10 um to 1 mm, with gaps of 1 nm to 1 mm therebetween in both the widthwise direction (d1) and the lengthwise direction (d2). The sensing chip 1 may be designed to amplify a specific frequency by adjusting the material of the meta unit 11 and/or the spec of the pattern 111 to set the resonance transmission frequencies of the sensing chip 1. Concrete examples are described, below.

In a particular embodiment of the present disclosure, the substrate 12, positioned beneath one side of the meta unit 11 to support the meta unit 11, is made of a transparent material, such as quartz, silicon, sapphire, glass, etc.

The irradiator irradiates onto the sensing chip 1 terahertz electromagnetic waves with a frequency of, for example, 0.1 to 5 THz. The detector is provided for measuring a transmittance and/or a frequency change of the terawaves passing through the sensing chip 1 to specify sugars and to determine concentrations of the specified sugars. After the sensing chip 1 is positioned on the skin beneath which a vessel runs or a sample is loaded on the meta unit 11 of the sensing chip 1, terawaves are irradiated from the irradiator onto the sensing chip 1, and the detector measures the transmittance or frequency change of the terawaves passing through the sensing chip 1 to specify sugars and to determine concentrations of the specified sugars.

Turning to the method for sensing sugars using the device described above, it comprises a target preparation step in which a sugar of interest is distributed on a sensing chip 1 having a meta unit 11 in which a pattern is formed for selectively amplifying a specific frequency, a light irradiation step in which terahertz electromagnetic waves are irradiated to the sugar of interest on the meta unit 11, and a sugar determination step in which the terahertz electromagnetic waves passing through the sensing chip 1 are measured for transmittance or frequency change to specify sugars and to determine concentrations of the specified sugars.

The target preparation step is a step in which a sugar of interest (sample) is distributed on the sensing chip 1 having the meta unit 11 in which a pattern is formed for selectively amplifying a specific frequency. Sugars to be analyzed are distributed on the meta unit 11 of the sensing chip 1 through which a resonant transmission frequency corresponding to the absorption frequency of a sugar of interest is emitted. In the target preparation step, for example, if fructose is a target sugar, a sample such as a blood, a beverage, etc., is placed on the meta unit 11 of the sensing chip 1 from which a resonant transmission frequency identical or corresponding to the absorption frequency (1.7 THz) of fructose. To measure the concentration of D-glucose in a sample, a sample is distributed on the meta unit 11 of the sensing chip 1 from which a resonant transmission frequency corresponding to the absorption frequency of glucose (1.43 THz) is emitted. As mentioned above, the resonant transmission frequency of the sensing chip 1 can be readily adjusted according to the pattern of the meta unit 11. In the target preparation step, samples are placed on sensing chips 1 that are respectively designed according to sugars to be analyzed.

In the light irradiation step, terahertz electromagnetic waves are irradiated onto the sample (sugars) on the meta unit 11. In this regard, the irradiator emits a terawave with a frequency of 0.1 to 5 THz.

Figure 4:
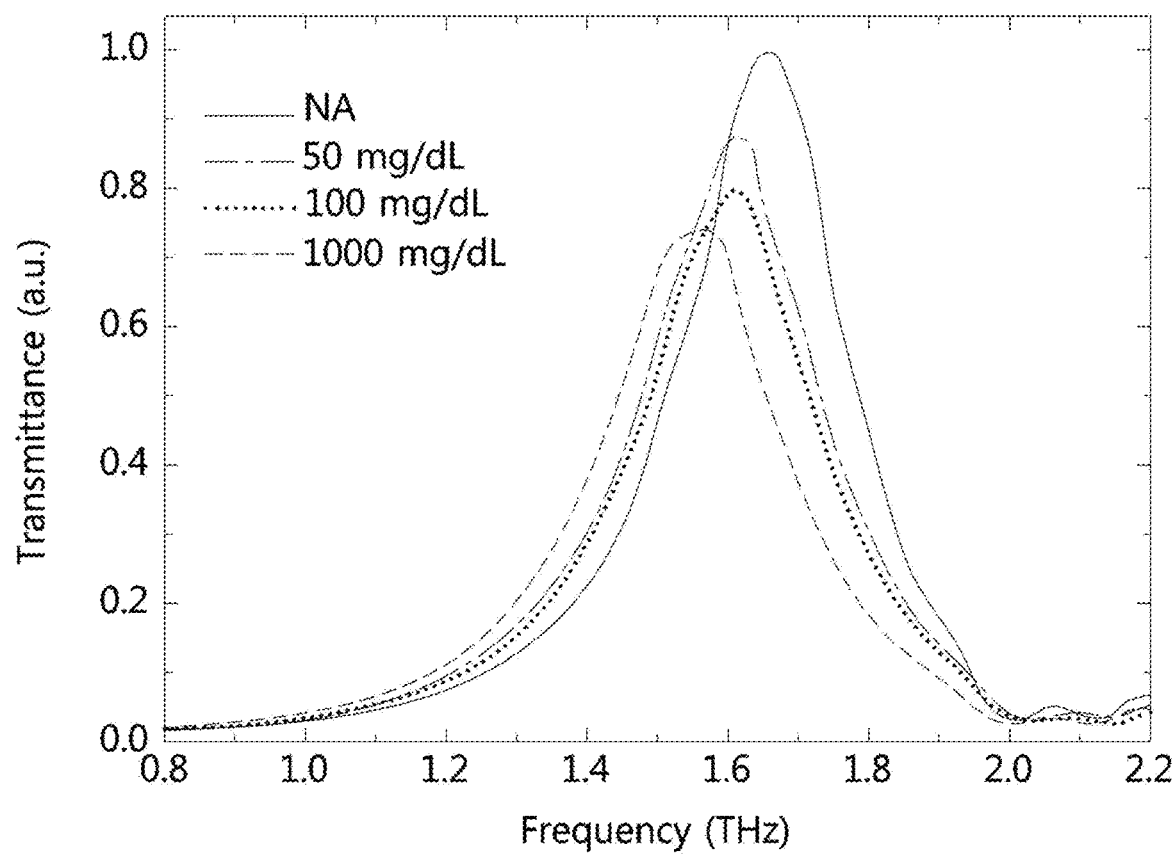
FIG. 4 is a graph showing measurement results of fructose obtained by using the sensing method of FIG. 1.
Figure 5:
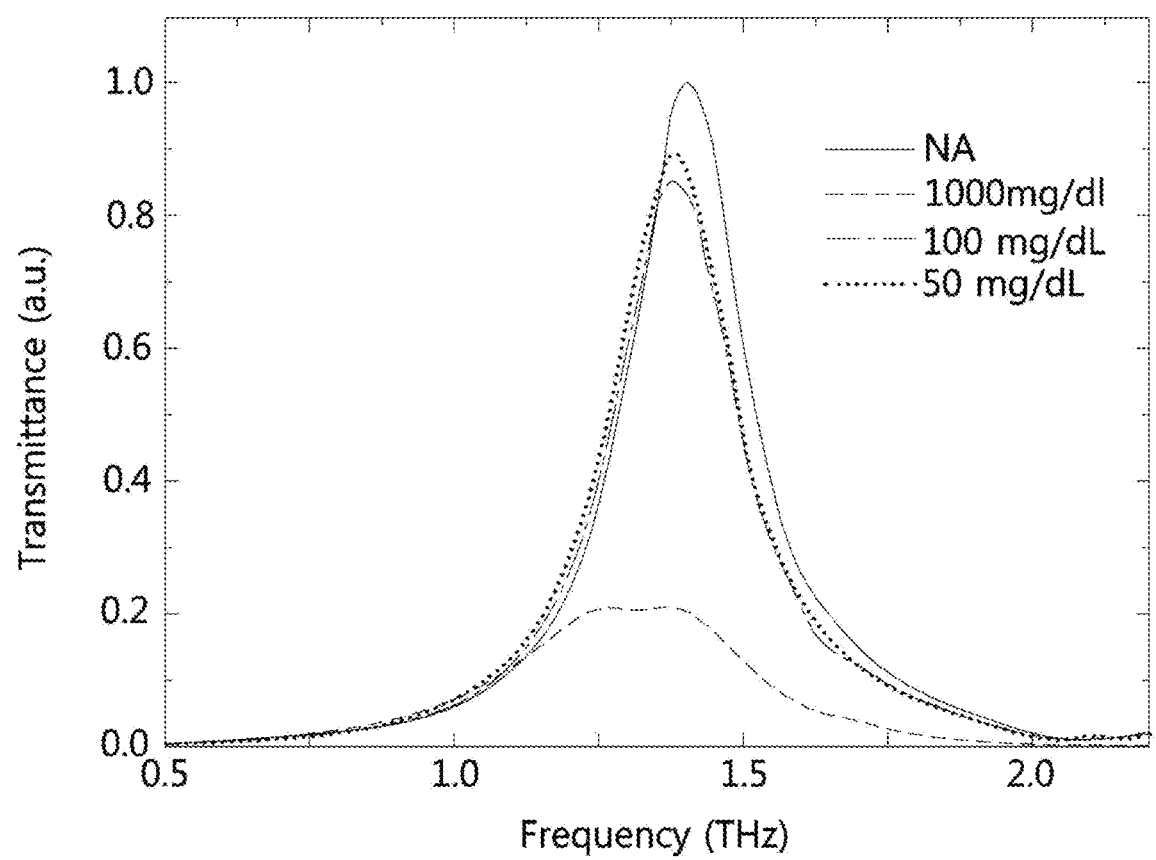
FIG. 5 is a graph showing measurement results of glucose obtained by using the sensing method of FIG. 1.
Figure 6:
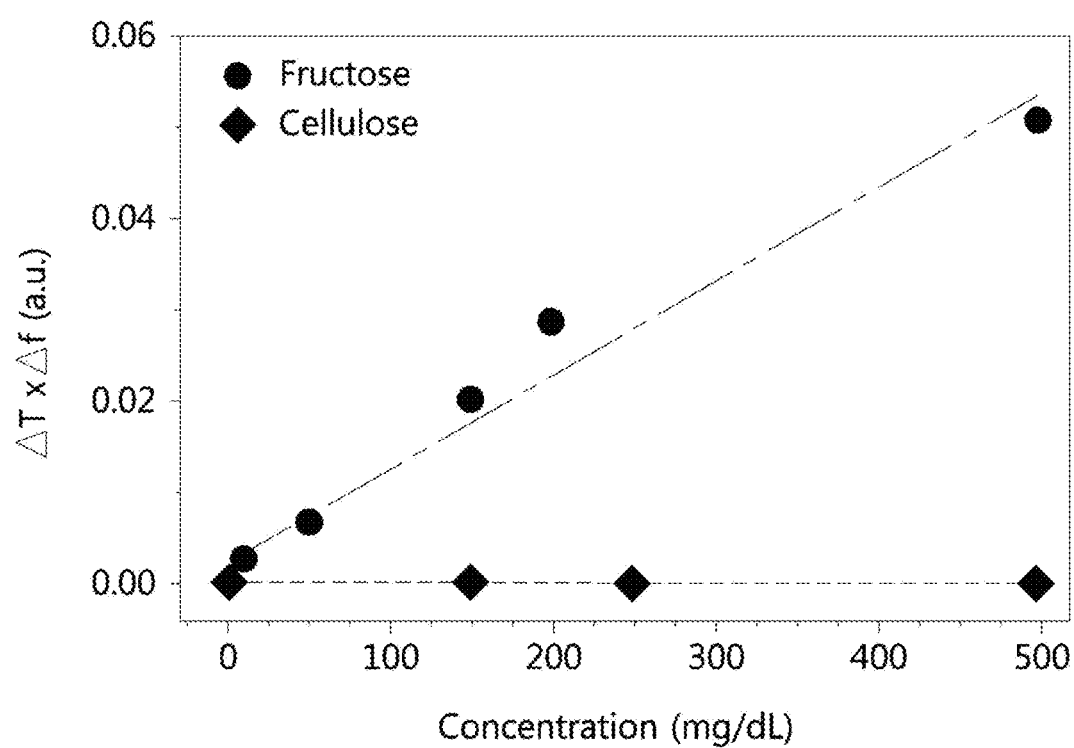
FIG. 6 is a graph explaining a method of specifying a sugar and determining a concentration of the specified sugar using the sensing method of FIG. 1.

In the sugar determination step, the terahertz electromagnetic waves passing through the sensing chip 1 are measured for transmittance or frequency change to specify sugars and to determine concentrations of the specified sugars. Based on the fact that transmittance or frequency change is elevated when the absorption frequency of a target sugar corresponds to the resonant transmission frequency of the meta unit, sugars can be analyzed for kind and concentration. By way of example, a sensing chip (substrate made of silicon 500 um thick, a meta unit made of gold 130 nm thick, and a pattern 500 nm wide, 35 um long, and 140 nm thick) was manufactured to emit a resonant transmission frequency corresponding to the absorption frequency of fructose, and one drop of a sample (comprising a buffer (PBS) and 50, 100, or 1000 mg/dL fructose) was added onto the meta unit 11 of the sensing chip 1. Then, terawaves were irradiated onto the sample, followed by measuring the transmittance and frequency change of the terawaves passing through the sensing chip 1. The measurement results are depicted in FIG. 4 (in which NA accounts for terawaves that were irradiated onto the sensing chip 1 with no samples placed on the chip). As can be seen in FIG. 4, the transmittance and the frequency vary with the concentration of fructose. In another example, a sensing chip (substrate made of silicon 500 um thick, a meta unit made of gold 130 nm thick, and a pattern 500 nm wide, 40 um long, and 130 nm thick) was manufactured to emit a resonant transmission frequency corresponding to the absorption frequency of D-glucose, and one drop of a sample (comprising a buffer (PBS) and 50, 100, or 1000 mg/dL glucose) was added onto the meta unit 11 of the sensing chip 1. Then, terawaves were irradiated onto the sample, followed by measuring the transmittance and frequency change of the terawaves passing through the sensing chip 1. The measurement results are depicted in FIG. 5. As can be seen in FIG. 5, the transmittance and the frequency vary with the concentration of glucose. In a further example, a sensing chip was manufactured to emit a resonant transmission frequency corresponding to the absorption frequency of fructose, and one drop of a sample (comprising fructose and cellulose, each ranging in concentration from 0 to 500 mg/dL, plus a buffer (PBS)) was added onto the meta unit 11 of the sensing chip 1. Then, terawaves were irradiated onto the sample, followed by measuring the transmittance and frequency change of the terawaves passing through the sensing chip 1. Results of transmittance change ($\Delta T$) x frequency position (peak) shift ($\Delta f$) are plotted against concentrations, and are depicted in FIG. 6. As can be seen in FIG. 6, the waves emitted from the sensing chip 1 exhibit large transmittance changes and frequency shifts in correspondence to the absorption frequency of fructose. For cellulose, only very small transmittance changes and frequency shifts are observed because the waves emitted from the sensing chip 1 do not correspond to the absorption frequency of cellulose. Accordingly, when terawaves are irradiated onto a sample placed on a sensing chip that can emit a resonant transmission frequency corresponding to an absorption frequency of a target sugar, a specific terawave is amplified from the sensing chip, with the concomitant generation of a large transmittance change and frequency shift. In addition, the transmittance and the frequency vary with the concentration of the sugar of interest. Thus, the magnitude of the transmittance and frequency shift of the terawave detected from the sensing chip allows for determining the kind and concentration of the sugar.

Capable of detecting even several micromoles of a subject in a liquid state, the method for sensing sugars is very sensitive. For example, a normal person has a blood sugar concentration of 100 mg/dL, which is converted into a molar concentration of about 5.5 mM, while a diabetes patient has a blood sugar concentration of as high as 200 mg/dL, which is converted into a molar concentration of 11.0 mM. Hence, a blood can be used, as it is, in measuring measure blood sugar levels by the sensing method of the present disclosure. In addition, the sensing method can selectively measure concentrations of as high as tens to hundreds mM of fructose and artificial sweeteners (aspartame, acesulfame K, etc.) in commercially available beverages. That is, the method can be used to measure very low concentration of sugars in foods such as beverages.

In accordance with another embodiment thereof, the present disclosure addresses a method for sensing sugars, comprising a chip disposition step in which the sensing chip 1 having a meta unit 11 provided with a pattern for selectively amplifying a specific frequency is positioned on the skin beneath which a vessel runs, a light irradiation step in which terahertz electromagnetic waves are irradiated onto the vessel through the sensing chip, and a sugar determination step in which terahertz electromagnetic waves that are reflected from blood of the vessel and pass through the sensing chip 1 are measured for transmittance or frequency change to specify sugars and to determine concentrations of the specified sugars. From the aforementioned method in which a sample (sugars) is dropped on the meta unit 11 and terawaves are irradiated, followed by detecting the transmittance and frequency shift of the terawaves passing the sensing chip 1, this method is different only in the steps of positioning the sensing chip 1 on the skin beneath which a vessel runs, irradiating terawaves the vessel through the sensing chip 1, and detecting the transmittance and frequency shift of terawaves that are reflected from the blood of the vessel through the sensing chip 1 so as to specify a sugar and to determine the concentration of the specified sugar. The two methods are based on the same principle that a sensing chip from which a resonant transmission frequency corresponding to an absorption frequency of a sugar of interest can be emitted is utilized to specify a sugar and determine the concentration of the sugar through the amplification of terawaves. Hence, a detailed description relevant to the principle is omitted.

As described in the foregoing embodiments and constitutional elements of the present disclosure, and their combinations, the present invention enjoys the following advantages.

The method and device according to the present invention can accurately discriminate and sense even a trace amount of sugars in a liquid state, with high sensitivity and selectivity, using a sensing chip that works in a terahertz electromagnetic wave band.

Also, capable of irradiating terahertz electromagnetic waves onto sugar through a sensing chip having a meta unit in which a pattern is formed to amplify a frequency corresponding to an absorption frequency of a sugar of interest, the method and device according to the present invention can accurately analyzing sugars even at low concentrations, with high sensitivity and selectivity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for sensitively and selectively sensing sugars, using a sensing chip, comprising:
   applying a sample to be analyzed on the sensing chip having a meta device,
   wherein the meta device includes a pattern in a form of slits that serves to amplify a frequency corresponding to an absorption frequency of a sugar of interest;
   irradiating the sensor chip with terahertz electromagnetic waves;
   amplifying waves reflected from the sample;
   measuring the terahertz electromagnetic waves reflected from the sugar in the sample by frequency change of the terahertz electromagnetic waves;
   determining a type of the sugar of interest using the measurement of terahertz electromagnetic waves; and
   determining the type and concentration of the sample of the specified sugars, based on the fact that the frequency change is elevated when the absorption frequency of the target sugar of interest corresponds to a resonant transmission frequency of the meta device; and
   analyzing the sugar of interest for type and concentration based on the determination of the type and concentration of the sample of the specified sugars.

2. The method of claim 1, wherein the method comprises:
   a chip disposition step in which the sensing chip having the meta device in which a pattern is formed for selectively amplifying a specific frequency corresponding to the absorption of the sugar of interest is positioned on the skin beneath which a vessel runs;
   a light irradiation step in which terahertz electromagnetic waves are irradiated onto the vessel through the sensing chip; and
   a sugar determination step in which terahertz electromagnetic waves that are reflected from blood of the vessel and pass through the sensing chip are measured for frequency change to specify sugars and to determine concentrations of the specified sugars.

3. The method of claim 1, wherein the pattern is in a form of slits, each penetrating through the meta device.

4. The method of claim 3, wherein each of the slits ranges in width from 10 nm to 1 um, in thickness from 100 nm to 1 um, and in length from 10 um to 1 mm.

5. The method of claim 3, wherein the pattern is an array of slits that is formed at regular gaps in the meta device.

6. The method of claim 5, wherein the slits in the array are arranged at regular gaps of 1 nm to 1 mm in a widthwise direction and 1 nm to 1 mm in a lengthwise direction.

7. A device for sensing sugars, the device comprising:
   a transparent substrate that transmits terahertz electromagnetic waves therethrough; and
   a sensing chip having a meta device configured to determine a type and concentration of the sample of the specified sugars, based on the fact that the frequency change is elevated when the absorption frequency of the target sugar of interest corresponds to a resonant transmission frequency of the meta device, positioned on one side of the substrate, in which a pattern is formed to selectively amplify a frequency corresponding to an absorption frequency of a sugar of interest.

8. The device of claim 7, wherein the pattern is in a form of slits, each penetrating through the meta device.

9. The device of claim 8, wherein each of the slits ranges in width from 10 nm to 1 um, in thickness from 100 nm to 1 um, and in length from 10 urn to 1 mm.

10. The device of claim 8, wherein the pattern is an array of slits that is formed at regular gaps in the meta device.

11. The method of claim 10, wherein the slits in the array are arranged at regular gaps of 1 nm to 1 mm in a widthwise direction and 1 nm to 1 mm in a lengthwise direction.

* * * * *